United States Patent
Goka et al.

(10) Patent No.: US 9,759,593 B2
(45) Date of Patent: Sep. 12, 2017

(54) AIRFLOW-RATE DETECTING DEVICE CAPABLE OF DETECTING HUMIDITY

(71) Applicant: DENSO CORPORATION, Kariya, Aichi-pref. (JP)

(72) Inventors: Yasushi Goka, Kariya (JP); Takashi Ooga, Kariya (JP); Akiyuki Sudou, Takahama (JP); Junzo Yamaguchi, Nagoya (JP)

(73) Assignee: DENSO CORPORATION, Kariya (JP)

( * ) Notice: Subject to any disclaimer, the term of this patent is extended or adjusted under 35 U.S.C. 154(b) by 129 days.

(21) Appl. No.: 14/730,525

(22) Filed: Jun. 4, 2015

(65) Prior Publication Data

US 2015/0355009 A1  Dec. 10, 2015

(30) Foreign Application Priority Data

Jun. 6, 2014 (JP) .................. 2014-117318

(51) Int. Cl.
| | |
|---|---|
| *G01F 5/00* | (2006.01) |
| *G01F 15/00* | (2006.01) |
| *G01N 33/00* | (2006.01) |
| *G01F 1/684* | (2006.01) |

(52) U.S. Cl.
CPC .............. *G01F 5/00* (2013.01); *G01F 1/6842* (2013.01); *G01F 15/00* (2013.01); *G01N 33/00* (2013.01)

(58) Field of Classification Search
None
See application file for complete search history.

(56) References Cited

U.S. PATENT DOCUMENTS

| 7,520,051 B2 * | 4/2009 | Becke ..................... G01F 1/684 29/832 |
| 2009/0293636 A1 | 12/2009 | Uchiyama et al. |
| 2010/0031737 A1 | 2/2010 | Saito et al. |
| 2012/0079879 A1 | 4/2012 | Saito et al. |
| 2012/0085324 A1 * | 4/2012 | Saito ......................... G01F 5/00 123/494 |
| 2012/0198925 A1 | 8/2012 | Saito et al. |
| 2013/0019675 A1 | 1/2013 | Ban et al. |
| 2013/0036806 A1 | 2/2013 | Kohno |
| 2016/0097661 A1 * | 4/2016 | Hidaka ..................... G01F 1/34 73/114.33 |

FOREIGN PATENT DOCUMENTS

| JP | 2014010026 A  * | 1/2014 |
| JP | 2015-090338 | 5/2015 |

* cited by examiner

*Primary Examiner* — Daniel J Colilla
(74) *Attorney, Agent, or Firm* — Nixon & Vanderhye P.C.

(57) ABSTRACT

An airflow-rate detecting device capable of detecting humidity has a housing, a flow rate sensor, a humidity sensor, a humidity sensor case, and a dust separating portion. The housing therein defines a bypass passage into which a part of air flowing in a duct flows. The flow rate sensor is disposed in the bypass passage. The humidity sensor detects a humidity of air flowing in the duct at an outside of the housing. The humidity sensor case houses the humidity sensor and therein defines an interior space into which a part of air flowing in the duct flows as a target air of which humidity is detected by the humidity sensor. The dust separating portion removes dust from the target air before the target air flows into the interior space.

10 Claims, 12 Drawing Sheets

AIRFLOW-RATE DETECTING DEVICE CAPABLE OF DETECTING HUMIDITY

CROSS REFERENCE TO RELATED APPLICATION

This application is based on Japanese Patent Application No. 2014-117318 filed on Jun. 6, 2014, the disclosure of which is incorporated herein by reference in its entirety.

TECHNICAL FIELD

The present disclosure relates to an airflow-rate detecting device capable of detecting humidity.

BACKGROUND

Conventionally, an airflow-rate detecting device capable of detecting humidity is known to have a constitution as described in Patent Documents 1 and 2, or the like.

Patent Document 1 (JP 5178388 B2) describes an airflow-rate detecting device having a flow rate sensor and a humidity sensor. The flow rate sensor is disposed in an auxiliary air passage in which a part of intake air flows. The humidity sensor is disposed in a second auxiliary air passage that is open in the auxiliary air passage. That is, air flowing in the auxiliary air passage is branched on an upstream side of the flow rate sensor such that the flow rate sensor and the humidity sensor are disposed in different airflows.

However, in the flow rate detector of Patent Document 1, air turbulence causes, and accuracy of flow rate detection may decrease.

Patent Document 2 (JP 2013-036892 A) describes an airflow-rate detecting device having a housing, a flow rate sensor, and a humidity sensor. The housing has a bypass passage in which a part of intake air flows. The flow rate sensor is disposed in the bypass passage. The humidity sensor is disposed to protrude from the housing into a duct in which intake-air flows. Accordingly, a location of the humidity sensor may not have an effect on accuracy of flow rate detection.

However, in the flow rate detector of Patent Document 2, dust included in intake air adheres to the humidity sensor easily, and dust adhering to the humidity sensor may affect accuracy of flow rate detection.

SUMMARY

The present disclosure addresses at least one of the above issues. Thus, it is an objective of the present disclosure to provide an airflow-rate detecting device capable of detecting humidity with which an adhesion of dust to a humidity sensor can be suppressed.

An airflow-rate detecting device capable of detecting humidity of the present disclosure has a housing, a flow rate sensor, a humidity sensor, a humidity sensor case, and a dust separating portion. The housing therein defines a bypass passage into which a part of air flowing in a duct flows. The flow rate sensor is disposed in the bypass passage. The humidity sensor detects a humidity of air flowing in the duct at an outside of the housing. The humidity sensor case houses the humidity sensor and therein defines an interior space into which a part of air flowing in the duct flows as a target air of which humidity is detected by the humidity sensor. The dust separating portion removes dust from the target air before the target air flows into the interior space. Since the dust separating portion is disposed in the airflow-rate detecting device, dust is prevented from flowing into the interior space in which the humidity sensor is disposed.

BRIEF DESCRIPTION OF THE DRAWINGS

The above and other objects, features and advantages of the present disclosure will become more apparent from the following detailed description made with reference to the accompanying drawings. In the drawings.

DETAILED DESCRIPTION

Figure 1:
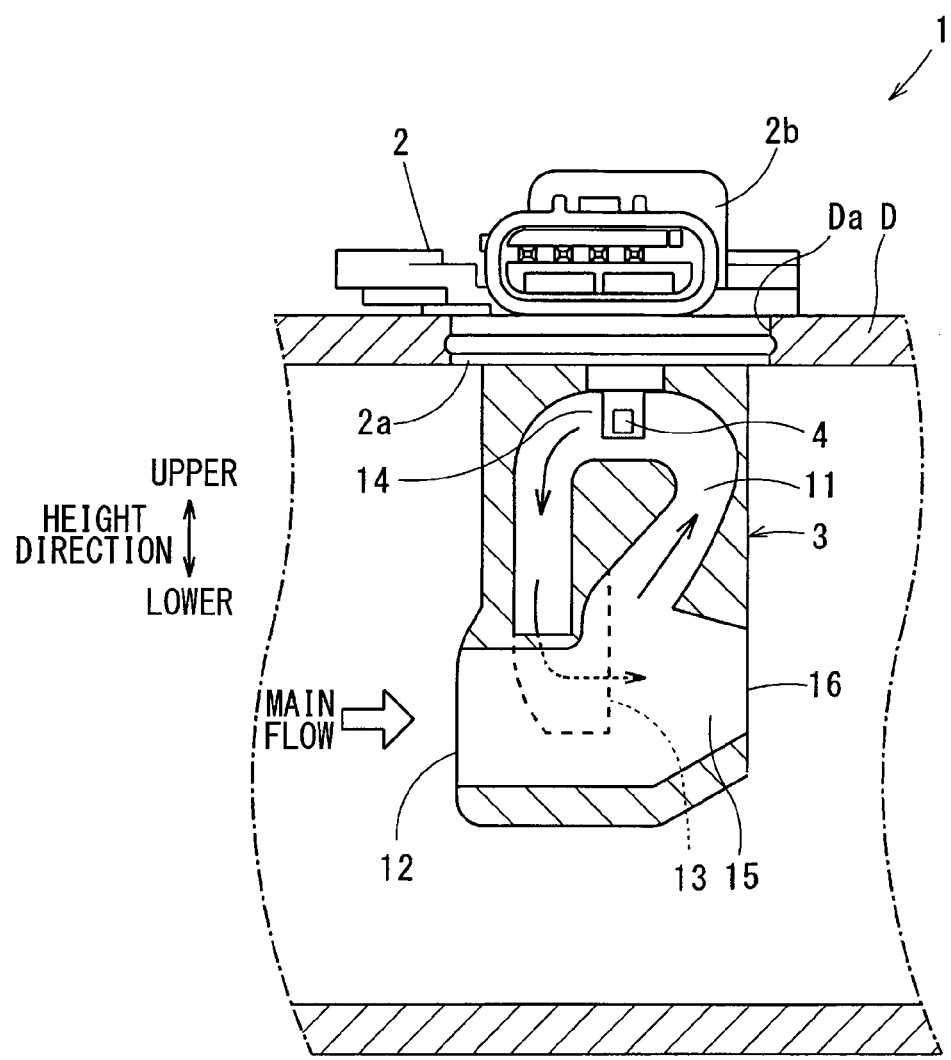
FIG. 1 is a cross-sectional view illustrating an airflow-rate detecting device regarding a first embodiment.

Embodiments of the present disclosure will be described hereafter referring to drawings. In the embodiments, a part that corresponds to a matter described in a preceding embodiment may be assigned with the same reference number, and redundant explanation for the part may be omitted. When only a part of a configuration is described in an embodiment, another preceding embodiment may be applied to the other parts of the configuration. The parts may be combined even if it is not explicitly described that the parts can be combined. The embodiments may be partially combined even if it is not explicitly described that the embodiments can be combined, provided there is no harm in the combination.

First Embodiment

A flow rate detector 1 for air capable of detecting humidity will be described hereafter referring to FIGS. 1 to 4. The flow rate detector 1 is, for example, an air flow meter detecting a volume of intake air taken into an internal combustion engine (i.e., an engine) for a vehicle. The flow rate detector 1 is attached to a duct D that is connected to a downstream side of an air cleaner. The duct D has an attachment hole Da defined in a wall of the duct D and having a circular shape. The flow rate detector 1 is inserted in the duct D from the attachment hole Da.

The flow rate detector 1 has a base portion 2, a housing 3, a flow rate sensor 4, a humidity sensor 5, and a humidity sensor case 6.

The base portion 2 has a fitting portion 2a fitting to the attachment hole Da and a connector housing 2b protruding radial-outward from the fitting portion 2a in a radial direction of the duct D. The fitting portion 2a has an outer surface facing an inner surface of the attachment hole Da. The outer surface has a groove into which an O-ring is disposed, and a clearance between the inner surface of the attachment hole Da and the outer surface of the fitting portion 2a is sealed gastightly by the O-ring (refer FIG. 1).

The housing 3 extends from the fitting portion 2a into the duct D and defines a bypass passage 11. A part of intake air flowing in the duct D flows into the bypass passage to be a target air. A main flow of air flowing in the duct D flows along a direction in which the duct D extends.

The direction along which the main flow flows will be referred to as a main flow direction hereafter. Further, a direction in which the housing 3 extends from the fitting portion 2a will be referred to as a height direction. A side on which the fitting portion 2a is located will be referred to as an upper side in the height direction, and a side opposite to the upper side in the height direction will be referred to as a lower side, hereafter, for an explanation purpose only. The housing 3 has a sidewall surface 3a extending in the height direction, and the main flow of air flows along the sidewall surface 3a.

The bypass passage 11 will be described hereafter.

The bypass passage 11 has a bypass inlet 12 and a bypass outlet 13. The bypass inlet 12 is open toward an upstream side in the main flow direction in the duct D. The bypass outlet 13 is open toward a downstream side in the main flow direction in the duct D. For example, air flowing into the bypass passage 11 from the bypass inlet 12 flows to the bypass outlet 13 after circulating in the housing 3 as shown in FIG. 1. The bypass passage 11 has an area 14 in which air flows in an opposite direction opposite to the main flow direction, and the flow rate sensor 4 is disposed in the area 14.

A dust emitting passage 15 is connected to the bypass passage 11 on an upstream side of the flow rate sensor 4. Dust flowing into the bypass passage 11 returns into the duct D from a dust emitting port 16 through the dust emitting passage 15 without flowing to the flow rate sensor 4.

Figure 3:
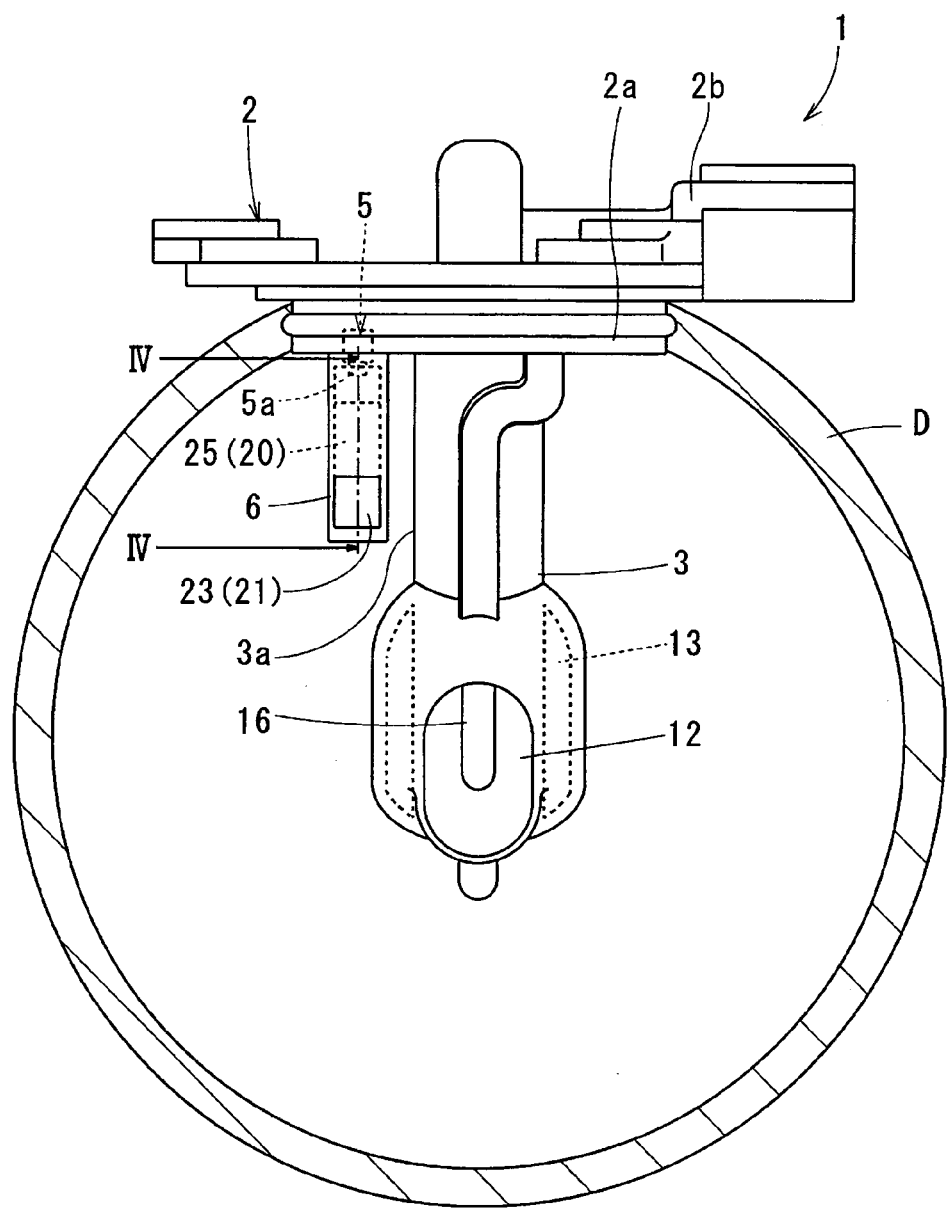
FIG. 3 is a view illustrating the flow rate detector when viewed from an upstream side in a main flow direction regarding the first embodiment.

The bypass outlet 13 is open toward the downstream side in the main flow direction, and air (i.e., fluid) flowing out of the bypass passage 11 from the bypass outlet 13 flows along the sidewall surface 3a. The bypass passage 11 branched into two passages on the downstream side of the flow rate sensor 4, and each of the two passages has the bypass outlet 13 as shown in FIG. 3. The two bypass outlets 13 are defined in an outer surface of the housing 3 to face to each other.

The flow rate sensor 4 outputs an electric signal such as a voltage signal depending on a flow rate (i.e., a flow volume) of air flowing in the bypass passage 11. Specifically, the base portion 2 houses a circuit board (not shown), and the circuit board is electrically connected with a heat generating element and a thermo-sensitive element. The heat generating element and the thermo-sensitive element are formed by a thin-film resistor member on a film (i.e., a membrane) provided on a semiconductor substrate.

The humidity sensor 5 outputs an electric signal such as a voltage signal depending on a detected humidity of air flowing in the duct D. The humidity sensor 5 uses, for example, a variation of a dielectric constant of a high polymer film that is caused by a variation of a relative humidity. The humidity sensor 5 has a sensing portion 5a provided with the high polymer film, a terminal connected to the sensing portion 5a, or the like.

Figure 2:
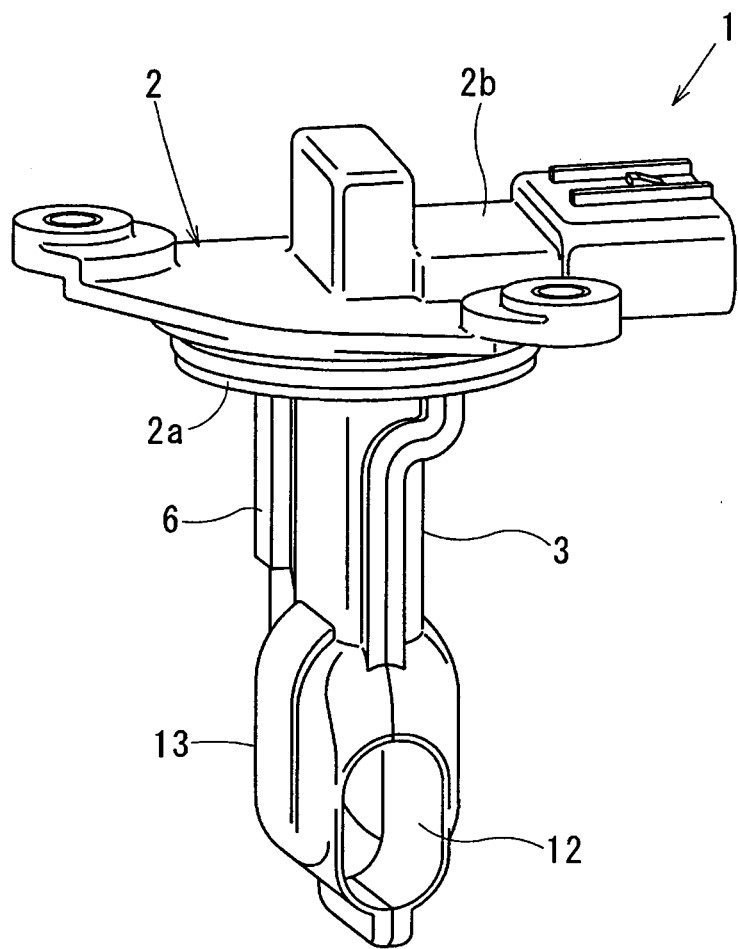
FIG. 2 is a perspective view illustrating the flow rate detector regarding the first embodiment.

The humidity sensor case 6 extends from the fitting portion 2a into the duct D and has an interior space 20. A part of air flowing in the duct D flows into the interior space 20 as a target air of which humidity is detected by the humidity sensor 5. The humidity sensor 5 is disposed such that the sensing portion 5a is exposed in the interior space 20. The humidity sensor case 6 is distanced from the sidewall surface 3a of the housing 3 in a direction perpendicular to the height direction as shown in FIGS. 2 and 3.

The humidity sensor case 6 has a dust separating portion 21 removing dust from air before the air flows into the interior space 20 such that air from which dust is removed flows into the interior space 20.

Figure 4:
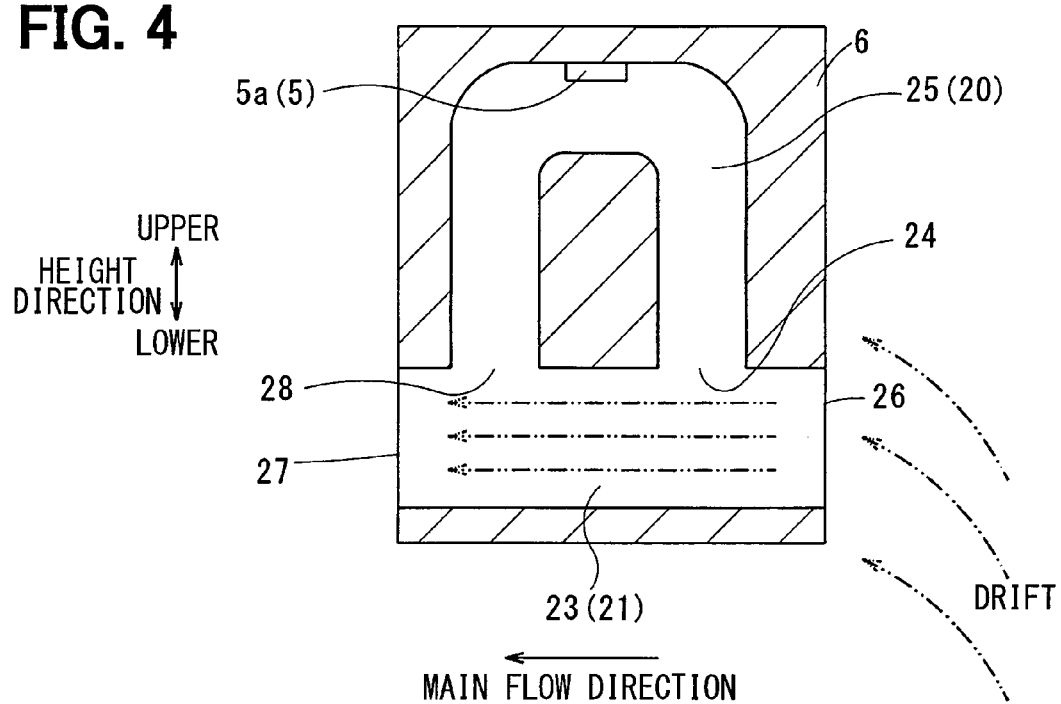
FIG. 4 is a cross-sectional view taken along a line IV-IV shown in FIG. 3.

The humidity sensor case 6 has a first passage 23 and a second passage 25 as shown in FIGS. 3 and 4. A part of air flowing in the duct D flows into the first passage 23. The second passage 25 has a branch inlet 24 opening in the first passage 23, and a part of air flowing in the first passage 23 flows into the second passage 25 from the branch inlet 24 as a target air of which humidity is detected by the humidity sensor 5.

The second passage 25 is defined as the interior space 20 in which the humidity sensor 5 is disposed, and the first passage 23 is defined as the dust separating portion 21. That is, dust is removed from the target air in a bifurcation area in which the second passage 25 is branched from the first passage 23, and dust removed from the target air flows in the first passage 23.

The first passage 23 extends in the main flow direction. Specifically, the first passage 23 extends generally straight in the main flow direction. The first passage 23 has an inlet 26 opening toward an upstream side in the main flow direction and an outlet 27 opening toward a downstream side in the main flow direction.

The second passage 25 is branched from the first passage 23 at the branch inlet 24 opening in an inner wall surface of the first passage 23. The second passage 25 has a branch outlet 28 opening in an inner wall surface of the first passage 23 such that air introduced from the branch inlet 24 returns to the first passage 23 through the branch outlet 28. The branch outlet 28 is located downstream of the branch inlet 24.

The branch inlet 24 and the branch outlet 28 open in a direction perpendicular to a flow direction (i.e., the main flow direction) of air flowing in the first passage 23. That is, an opening surface of the branch inlet 24 and an opening surface of the branch outlet 28 are defined to be parallel with the flow direction.

Dust included in air introduced into the first passage 23 flows along a flow of air flowing in the first passage 23 by inertia force. Accordingly, dust is removed from the target air in the bifurcation area in which the second passage 25 is branched from the first passage 23, and air after removing dust flows in the second passage 25.

Even when a flow of air in the duct D makes an angle with the main flow direction by a drift flow, it can be prevented that dust flows into the second passage 25 (i.e., the interior space 20) since a flow direction of dust is regulated by the first passage 23. Therefore, an adhesion of dust on the humidity sensor disposed in the interior space 20 can be suppressed. Thus, an accuracy of humidity detection by the humidity sensor 5 can be improved.

Figure 13:
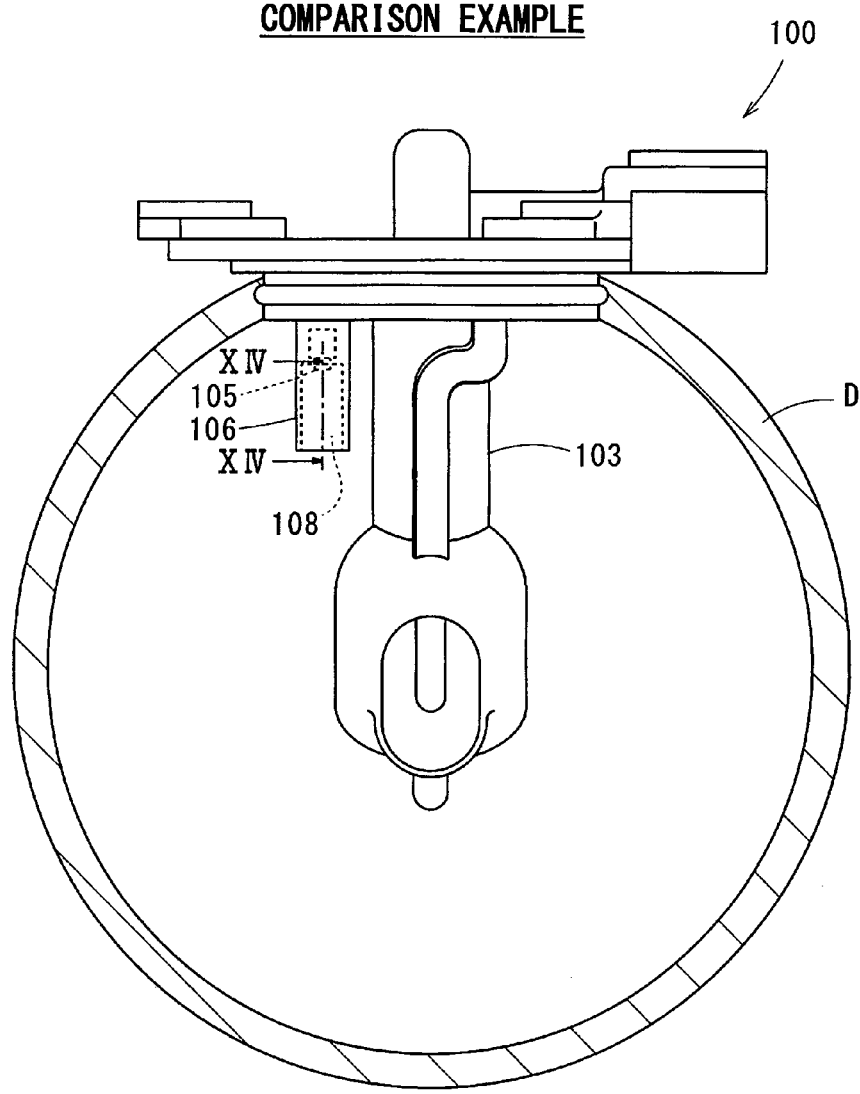
FIG. 13 is a view illustrating an airflow-rate detecting device when viewed from an upstream side in a main flow direction regarding a comparison example.
Figure 14:
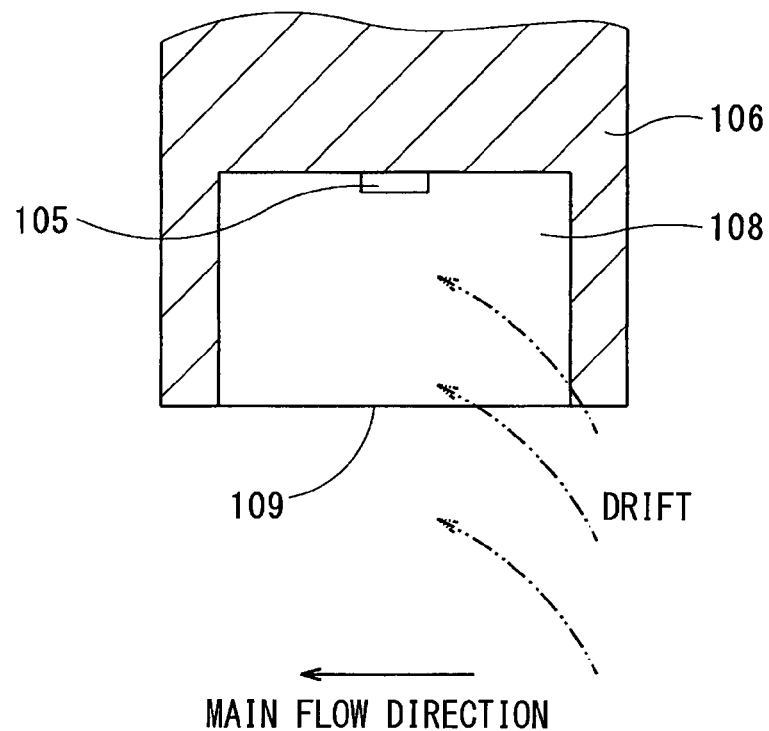
FIG. 14 is a cross-sectional view taken along a line XIV-XIV shown in FIG. 13.

In advance of the present disclosure, the inventors of the present disclosure made a flow rate detector 100 for air having a humidity sensor case 106 housing a humidity sensor 105 (JP Application No. 2013-230968). The flow rate detector 100 is shown in FIGS. 13 and 14 as a comparison example of the present disclosure, and it should be noted that the flow rate detector 100 is not a well-known flow rate detector. The flow rate detector 100 has a housing 103 therein having a bypass passage in which a flow rate sensor is disposed. The humidity sensor 105 is disposed to protrude from the housing 103 into a duct D in which intake air flows.

The humidity sensor case 106 defines an interior space 108 therein. A part of air flowing in the duct D flows into the interior space 108 to be a target air of which humidity is detected, and the humidity sensor 105 detects a humidity of the target air. The humidity sensor case 106 has an air inlet 109 opening in a direction that is generally perpendicular to a main flow direction. The main flow direction is a flow direction in which a main flow of air flows in the duct D and is parallel with a direction in which the duct D extends. Accordingly, the duct D has a structure with which less dynamic pressure is applied to the duct D by the main flow. Further, less dust adheres on the humidity sensor 105 as compared with Patent Document 2.

However, even in a case where the air inlet 109 is provided as described above, dust may come into the interior space 108 through the air inlet 109 when a drift causes in an airflow in the duct D (refer FIG. 14). The drift is caused, for example, by an air cleaner disposed on an upstream side of the flow rate detector 100 in an intake passage of an internal combustion engine. The drift may be caused when an element of the air cleaner is clogged. Alternatively, the drift may be caused due to a shape of the air cleaner.

Second Embodiment

A flow rate detector 1 for air of second embodiment will be described hereafter referring to FIG. 5. In the second embodiment, features changed with respect to the first embodiment will be described.

In the second embodiment, the first passage 23 has an inner surface 31 in which the branch inlet 24 is open. The inner surface 31 has a first protruding portion 33 protruding from the inner surface 31 into the first passage 23 at an upstream side of the branch inlet 24.

Figure 5:
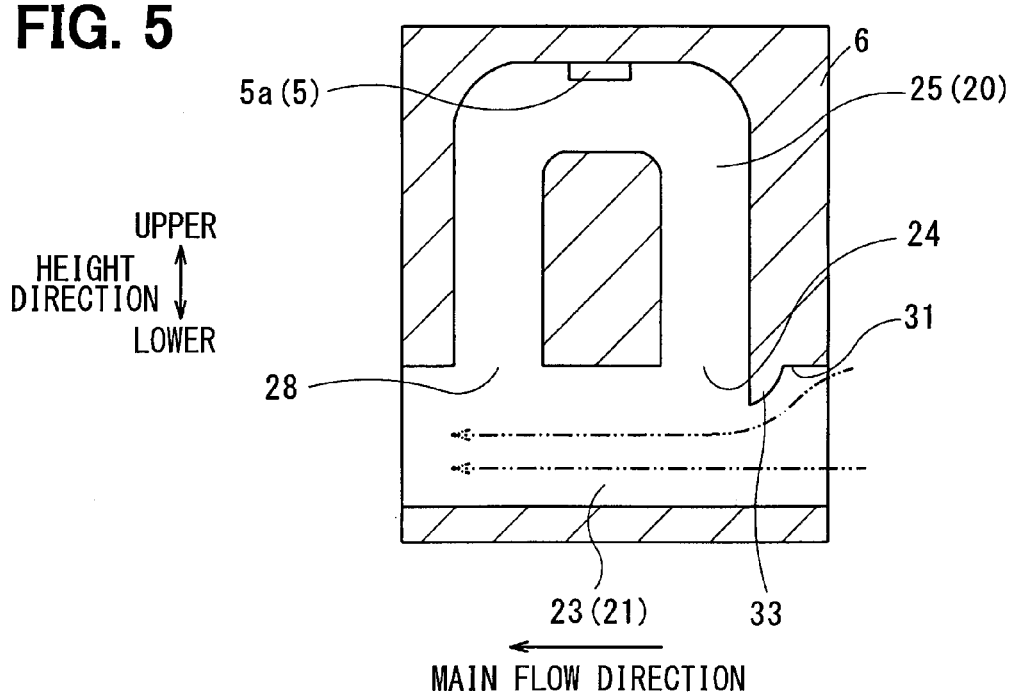
FIG. 5 is a cross-sectional view illustrating a part of an airflow-rate detecting device regarding a second embodiment.

Specifically, as shown in FIG. 5, the first protruding portion 33 is provided in an opening periphery of the branch inlet 24 on the upstream side of the branch inlet 24. The first protruding portion 33 protrudes downward, in other words, from the inner wall surface of the first passage 23 to an inside of the first passage 23.

Accordingly, air flowing in the first passage 23 can be controlled easily to flow in a direction away from the branch inlet 24. As a result, less amount of dust flows into the second passage 25 (i.e., the interior space 20) from the branch inlet 24. Moreover, dust can be prevented from flowing into the second passage 23 from the branch inlet 24 since dust collides with the first protruding portion 33.

Third Embodiment

Figure 6:
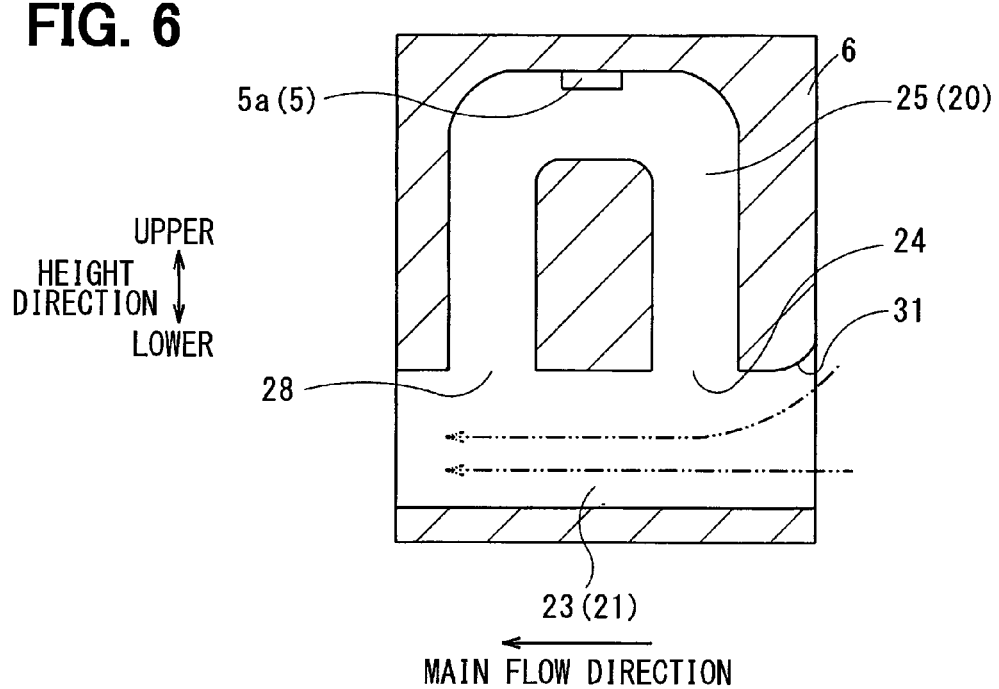
FIG. 6 is a cross-sectional view illustrating a part of an airflow-rate detecting device regarding a third embodiment.

A flow rate detector 1 for air of a third embodiment will be described hereafter referring to FIG. 6. In the third embodiment, features changed with respect to the first embodiment will be described.

In the third embodiment, the inner surface 31 has a shape that decreases a passage area of the first passage 23 from an upstream side to a downstream side on an upstream side of the branch inlet 24. Specifically, the inner surface 31 has a curved shape as shown in FIG. 6.

Accordingly, a flow of air flowing in the first passage 23 can be controlled easily to flow in a direction away from the branch inlet 24, similar to the second embodiment. Thus, less amount of dust flows into the second passage 25 from the branch inlet 24.

Fourth Embodiment

A flow rate detector 1 for air of a fourth embodiment will be described hereafter referring to FIG. 7. In the fourth embodiment, features changed with respect to the first embodiment will be described.

The inner surface 31 has a second protruding portion 34 protruding from the inner surface 31 into the first passage 23 on the downstream side of the branch inlet 24 and on an upstream side of the branch outlet 28.

Figure 7:
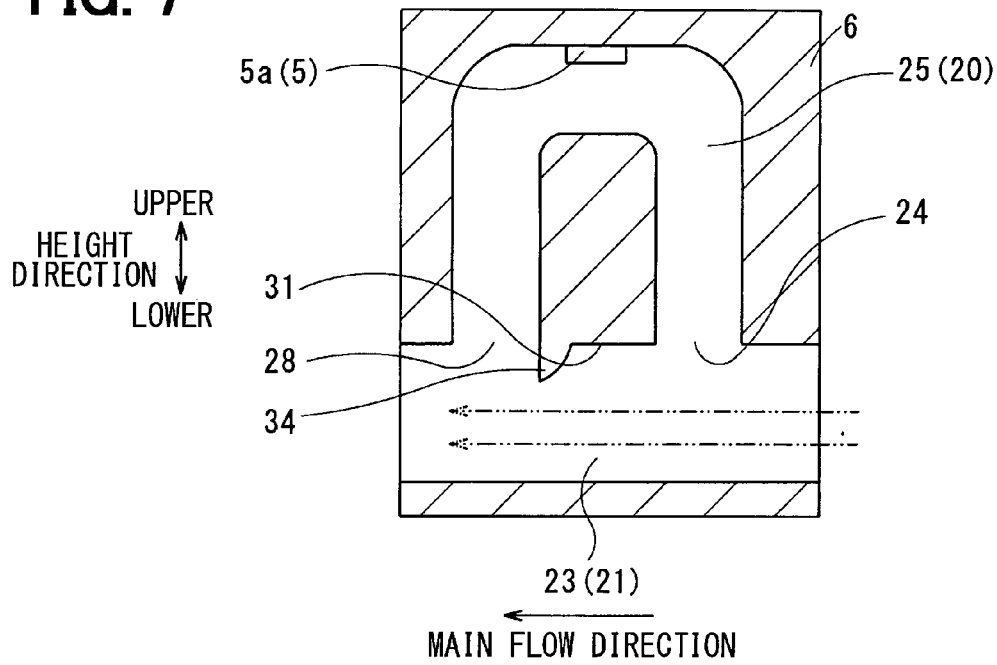
FIG. 7 is a cross-sectional view illustrating a part of an airflow-rate detecting device regarding a fourth embodiment.

Specifically, as shown in FIG. 7, the second protruding portion 34 is provided in the opening periphery of the branch inlet 24 on the upstream side of the branch outlet 28. The second protruding portion 34 protrudes downward, in other words, from the inner wall surface of the first passage 23 to an inside of the first passage 23.

As a result, although less amount of dust is removed from the target air as compared to the first to third embodiments, responsibility of the humidity sensor 5 improves since a flow amount of the target air flowing into the second passage 25 increases.

Fifth Embodiment

Figure 8:
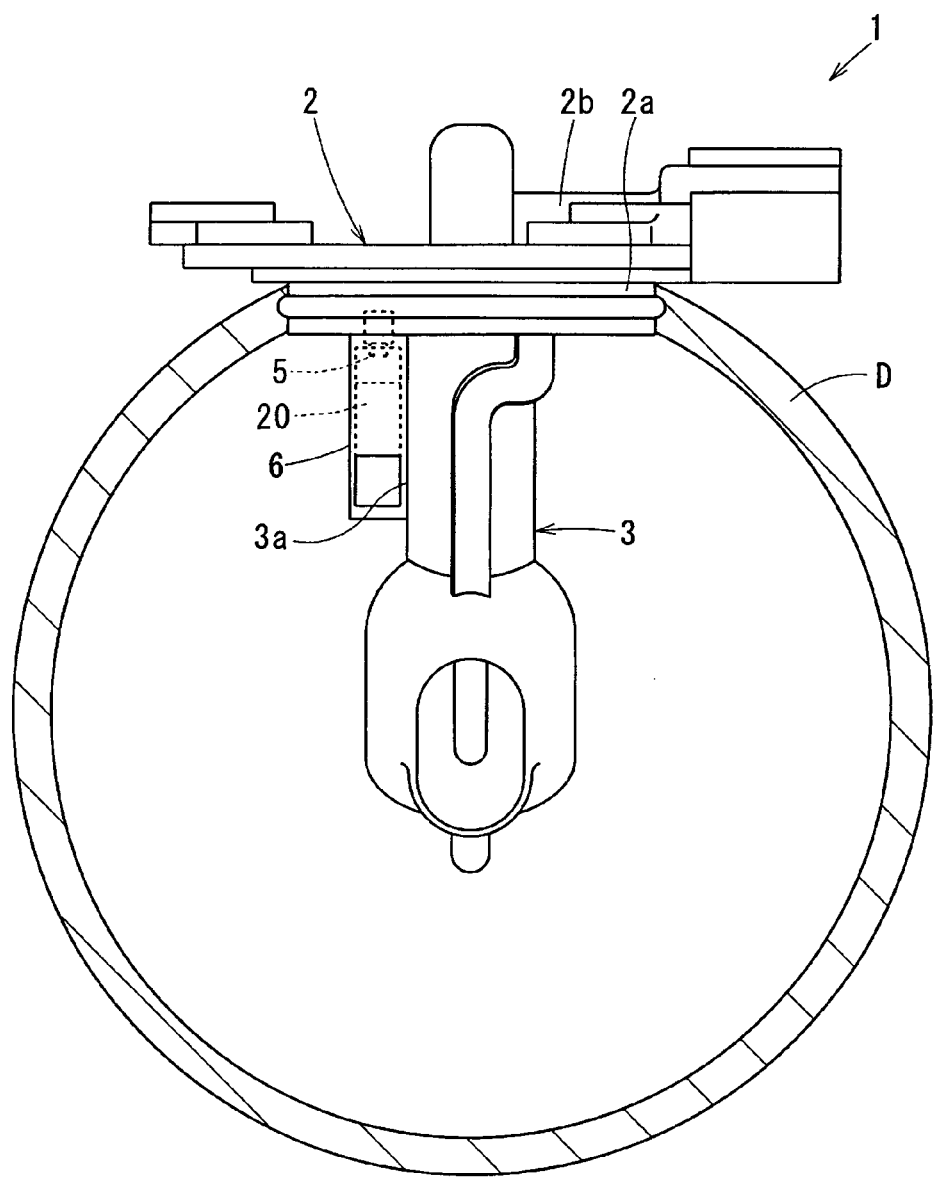
FIG. 8 is a view illustrating an airflow-rate detecting device when viewed from an upstream side in a main flow direction regarding a fifth embodiment.

A flow rate detector 1 for air of a fifth embodiment will be described hereafter referring to FIG. 8. In the fifth embodiment, features changed with respect to the first embodiment will be described.

In the fifth embodiment, the housing 3 and the humidity sensor case 6 are coupled with each other to be one piece, and protrude from the base portion 2 into the duct D.

In the first embodiment, the housing 3 and the humidity sensor case 6 protrude into the duct D in a state where the humidity sensor case 6 is distanced from the sidewall surface 3a of the housing 3 in the direction perpendicular to the height direction, in other words, in a direction perpendicular to the sidewall surface 3a.

In contrast, the humidity sensor case 6 of the present embodiment is not distanced from the sidewall surface 3a. Specifically, the humidity sensor case 6 of the present embodiment protrudes from the sidewall surface 3a of the housing 3. The housing 3 and the humidity sensor case 6 are made of resin integrally.

Thus, the same effects as the first embodiment can be produced by the present embodiment, and a quantity of components can be reduced.

Sixth Embodiment

Figure 9:
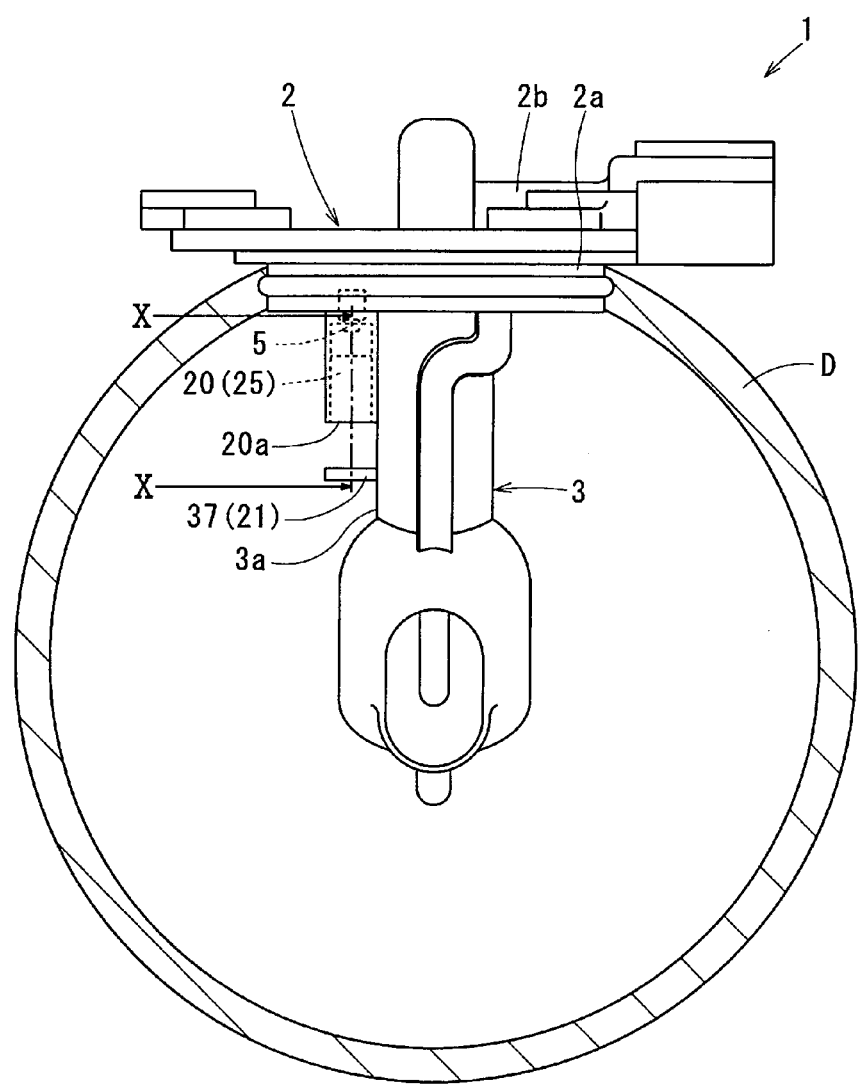
FIG. 9 is a view illustrating an airflow-rate detecting device when viewed from an upstream side in a main flow direction regarding a sixth embodiment.
Figure 10:
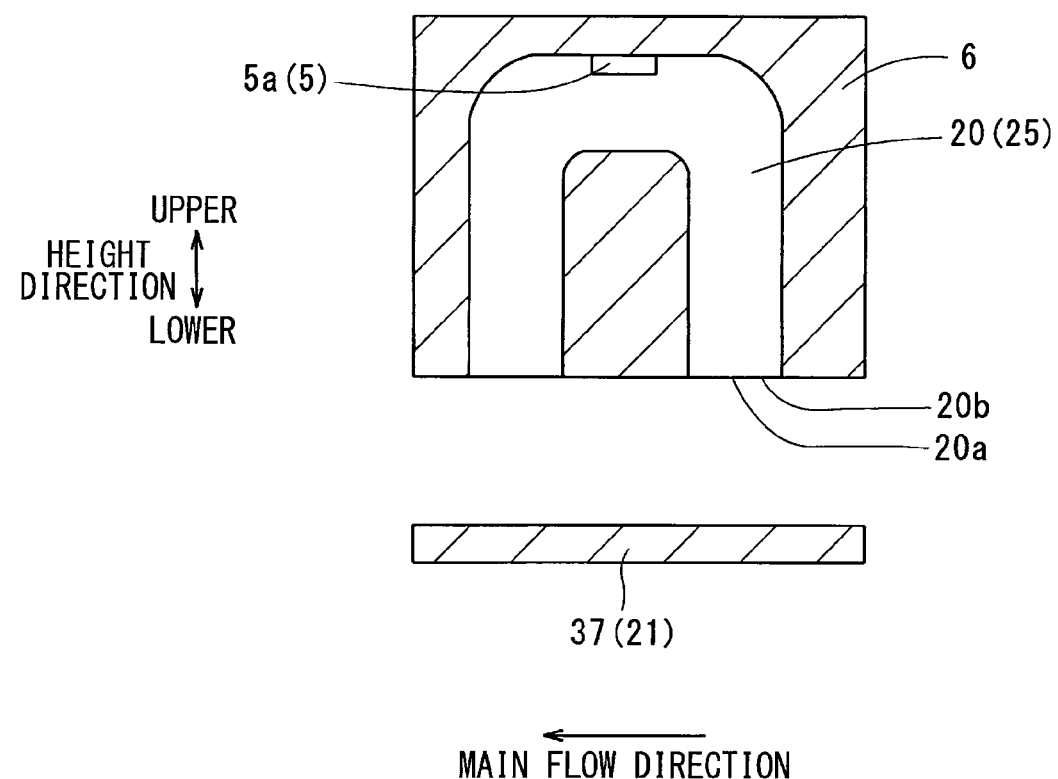
FIG. 10 is a cross-sectional view taken along a line X-X shown in FIG. 9.

A flow rate detector 1 for air of a sixth embodiment will be described hereafter referring to FIGS. 9 and 10. In the sixth embodiment, features changed with respect to the fifth embodiment will be described.

The flow rate detector 1 of the present embodiment has a current guiding board (i.e., a guiding portion) 37 instead of the first passage 23. The current guiding board 37 is located to face an aperture 20*b* of the branch inlet 24 (i.e., an air inlet portion 20*a*) of the second passage 25 from which the target air flows into the interior space 20.

That is, in the present embodiment, the air inlet portion 20*a* is open in a direction generally perpendicular to the main flow direction.

In the present embodiment, the current guiding board 37 is disposed as the dust separating portion 21 and guides air to flow in the duct D generally parallel with the main flow direction, in other words, generally parallel with the aperture 20*b*.

The current guiding board 37 protrudes from the sidewall surface 3*a* and extends in the main flow direction from an upstream side of the branch inlet 24 through a downstream side of the branch outlet 28.

Since the current guiding board 37 guides air to flow in the main flow direction in the duct D, a dust included in the air also flow in the main flow direction from the upstream side of the aperture 20*b* of the branch inlet 24 through the downstream side of the branch outlet 28. As a result, the dust can be restricted from flowing into the interior space 20 from the air inlet portion 20*a*.

Further, as compared to a case of having the first passage 23, a pressure loss occurred by the flow rate detector 1 in the duct D can be reduced.

Seventh Embodiment

A flow rate detector 1 for air of a seventh embodiment will be described hereafter referring to FIG. 11. In the seventh embodiment, features changed with respect to the sixth embodiment will be described.

In the present embodiment, the base portion 2 constitutes at least a part of the humidity sensor case 6, and at least a part of the interior space 20 is defined in the base portion 2.

Figure 11:
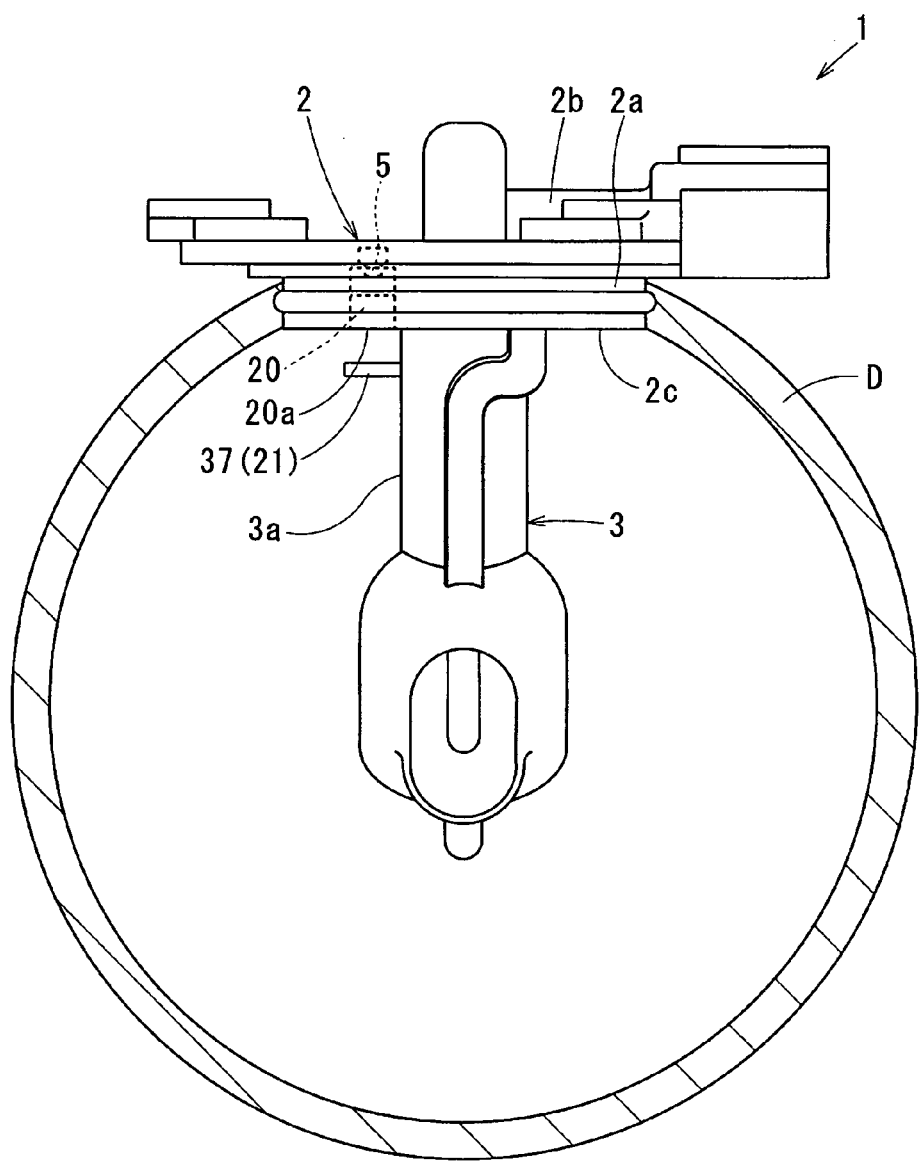
FIG. 11 is a view illustrating an airflow-rate detecting device when viewed from an upstream side in a main flow direction regarding a seventh embodiment.

For example, as shown in FIG. 11, the interior space 20 is defined inside of the base portion 2. The base portion 2 has a surface 2*c* exposed in the duct D, and the air inlet portion 20*a* is defined in the surface 2*c* such that air flows into the interior space 20 from the air inlet portion 20*a*.

Similar to the sixth embodiment, the current guiding board 37 protrudes from the sidewall surface 3*a* of the housing 3.

The seventh embodiment produces the same effects as the sixth embodiment. Moreover, since the base portion 2 provides a wall defining the interior space 20, a quantity of components can be reduced.

(Other Modifications)

Figure 12:
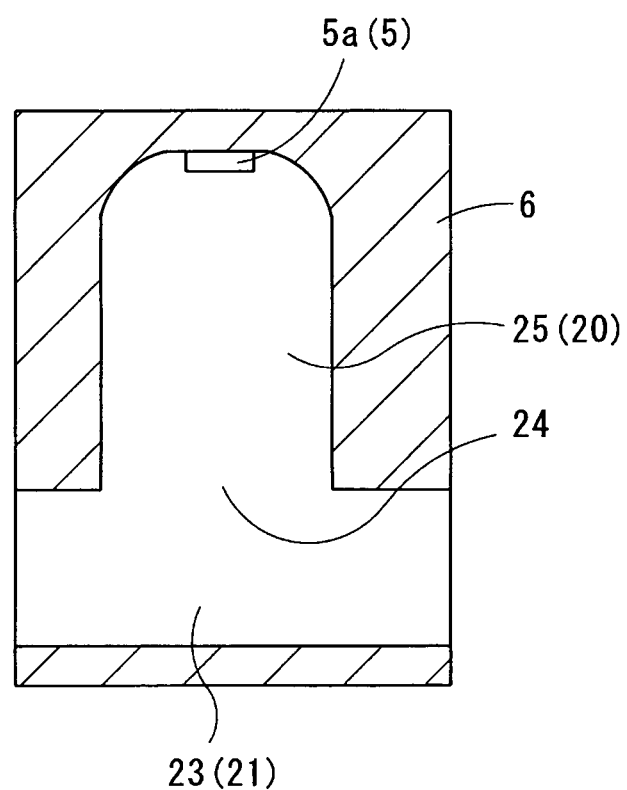
FIG. 12 is a view illustrating a part of an airflow-rate detecting device regarding a modification example.

In the above-described embodiment, the branch outlet 28 is defined in the inner wall surface of the first passage 23 such that air introduced in the second passage 25 from the branch inlet 24 returns to the first passage 23. However, a downstream end of the second passage 25 may be sealed. That is, the branch outlet 28 may not be necessary (refer FIG. 12). Even if the downstream end of the second passage 25 is sealed, dust can be separated.

In the above-described embodiment, the current guiding board 37 guides air to flow in a direction generally parallel with the main flow direction around the aperture 20*b* of the branch inlet 24 (i.e., the air inlet portion 20*a*). However, the current guiding board 37 may guide air to flow away from the air inlet portion 20*a*.

Such changes and modifications are to be understood as being within the scope of the present disclosure as defined by the appended claims.

What is claimed is:

1. An airflow-rate detecting device capable of detecting humidity, the airflow-rate detecting device comprising:
a housing therein defining a bypass passage into which a part of air flowing in a duct flows;
a flow rate sensor disposed in the bypass passage;
a humidity sensor detecting a humidity of air flowing in the duct at an outside of the housing;
a humidity sensor case housing the humidity sensor and therein defining an interior space into which a part of air flowing in the duct flows as a target air of which humidity is detected by the humidity sensor; and
a dust separating portion removing dust from the target air before the target air flows into the interior space, wherein
the humidity sensor case has a first passage into which a part of air flowing in the duct flows and a second passage branched from the first passage,
the second passage has a branch inlet from which a part of air flowing in the first passage flows into the second passage,
the first passage is provided as the dust separating portion,
the second passage is provided as the interior space, and
the first passage has a bifurcation area in which the second passage is branched from the first passage, and the dust flowing in the first passage is removed from the target air in the bifurcation area.

2. The airflow-rate detecting device capable of detecting humidity according to claim 1, wherein
the second passage has a branch outlet through which air flowing from the branch inlet flows out of the second passage into the first passage.

3. The airflow-rate detecting device capable of detecting humidity according to claim 2, wherein
the first passage has an inner wall surface in which the branch inlet is defined,
the branch outlet is defined in the inner wall surface on a downstream side of the branch inlet, and
the inner wall surface has a second protruding portion protruding from the inner wall surface into the first passage on a downstream side of the branch inlet and on an upstream side of the branch outlet.

4. The airflow-rate detecting device capable of detecting humidity according to claim 1, wherein
the first passage has an inner wall surface in which the branch inlet is defined, and
the inner wall surface has a first protruding portion protruding from the inner surface into the first passage on an upstream side of the branch inlet.

5. The airflow-rate detecting device capable of detecting humidity according to claim 1, wherein
the first passage has an inner wall surface in which the branch inlet is defined, and
the inner wall surface has a shape that decreases a passage area of the first passage from an upstream side toward a downstream side on an upstream side of the branch inlet.

6. The airflow-rate detecting device capably of detecting humidity according to claim 1, wherein
the duct extends in a main flow direction in which a main flow of air flows in the duct,
the interior space is defined with an air inlet portion opening in a direction generally perpendicular to the main flow direction, and air flows into the interior space from the air inlet portion, and the dust separating portion is disposed as a guiding portion that faces an aperture of the air inlet portion and guides air to flow generally parallel with the main flow direction.

7. The airflow-rate detecting device capable of detecting humidity according to claim 1, further comprising a base portion attached to the duct to fit to an attachment hole that is defined in a wall of the duct, wherein the housing and the humidity sensor case are coupled with each other and protrude from the base portion into the duct.

8. The airflow-rate detecting device capable of detecting humidity according to claim 1, further comprising a base portion attached to the duct to fit to an attachment hole that is defined in a wall of the duct, wherein the housing extends from the base portion into the duct, and the base portion configures at least a part of the humidity sensor case, and at least a part of the interior space is defined in the base portion.

9. The airflow-rate detecting device capable of detecting humidity according to claim 1, wherein the dust separating portion is provided in the humidity sensor case.

10. An airflow-rate detecting device capable of detecting humidity, the airflow-rate detecting device comprising:

a housing therein defining a bypass passage into which a part of air flowing in a duct flows;

a flow rate sensor disposed in the bypass passage;

a humidity sensor detecting a humidity of air flowing in the duct at an outside of the housing;

a humidity sensor case housing the humidity sensor and therein defining an interior space into which a part of air flowing in the duct flows as a target air of which humidity is detected by the humidity sensor; and a dust separating portion removing dust from the target air before the target air flows into the interior space; wherein the duct extends in a main flow direction in which a main flow of air flows in the duct, the interior space is defined with an air inlet portion opening in a direction generally perpendicular to the main flow direction, and air flows into the interior space from the air inlet portion, and the dust separating portion is disposed as a guiding portion that faces an aperture of the air inlet portion and guides air to flow generally parallel with the main flow direction.

* * * * *